US010815191B2

(12) United States Patent
Schwab et al.

(10) Patent No.: US 10,815,191 B2
(45) Date of Patent: Oct. 27, 2020

(54) FORMULATION COMPRISING ESTER QUATS BASED ON ISOPROPANOLAMINE AND TETRAHYDROXYPROPYL ETHYLENEDIAMINE

(71) Applicant: Evonik Degussa GmbH, Essen (DE)

(72) Inventors: Peter Schwab, Essen (DE); Hans-Juergen Koehle, Mainhausen (DE); Kurt Seidel, Jossgrund (DE); Ursula Westerholt, Essen (DE); Hans Henning Wenk, Muelheim an der Ruhr (DE)

(73) Assignee: EVONIK OPERATIONS GMBH, Essen (DE)

( * ) Notice: Subject to any disclaimer, the term of this patent is extended or adjusted under 35 U.S.C. 154(b) by 605 days.

(21) Appl. No.: 14/861,391

(22) Filed: Sep. 22, 2015

(65) Prior Publication Data

US 2016/0083333 A1 Mar. 24, 2016

(30) Foreign Application Priority Data

Sep. 22, 2014 (EP) .................................... 14185780

(51) Int. Cl.
*C07C 219/08* (2006.01)
*A61Q 5/06* (2006.01)
*A61Q 5/12* (2006.01)
*A61K 8/41* (2006.01)
*A61Q 5/02* (2006.01)
*A61K 8/45* (2006.01)
*C07C 219/06* (2006.01)
*A61Q 19/10* (2006.01)

(52) U.S. Cl.
CPC ............ *C07C 219/08* (2013.01); *A61K 8/416* (2013.01); *A61K 8/45* (2013.01); *A61Q 5/02* (2013.01); *A61Q 5/06* (2013.01); *A61Q 5/12* (2013.01); *C07C 219/06* (2013.01); *A61Q 19/10* (2013.01)

(58) Field of Classification Search
CPC ........ A61K 31/225; A61K 8/416; A61K 8/45; A61Q 5/06; A61Q 19/10; A61Q 5/12; A61Q 5/02; C07C 219/06; C07C 219/08
USPC ........................................................ 514/547
See application file for complete search history.

(56) References Cited

U.S. PATENT DOCUMENTS

| 4,789,491 | A | 12/1988 | Chang et al. |
|---|---|---|---|
| 5,180,508 | A | 1/1993 | Birkhan et al. |
| 5,364,542 | A | 11/1994 | Birkan et al. |
| 5,464,565 | A | 11/1995 | Hamann et al. |
| 5,681,972 | A | 10/1997 | Hamann et al. |
| 5,718,891 | A | 2/1998 | Prat et al. |
| 5,962,708 | A | 10/1999 | Hamann et al. |
| 6,110,887 | A | 8/2000 | Euler et al. |
| 6,180,593 | B1 | 1/2001 | Fender et al. |
| 6,180,594 | B1 | 1/2001 | Fender et al. |
| 6,242,499 | B1 | 6/2001 | Gruning et al. |
| 6,376,455 | B1 | 4/2002 | Friedli et al. |
| 6,653,275 | B1 | 11/2003 | Fender et al. |
| 7,074,419 | B2 | 7/2006 | Dietz et al. |
| 7,731,982 | B2 | 6/2010 | Schroeder |
| 7,847,123 | B2 | 12/2010 | Wenk et al. |
| 8,138,372 | B2 | 3/2012 | Herrwerth et al. |
| 8,211,972 | B2 | 7/2012 | Meyer et al. |
| 8,466,248 | B2 | 6/2013 | Meyer et al. |
| 8,563,499 | B2 | 10/2013 | Kohle et al. |
| 8,569,224 | B2 | 10/2013 | Kohle et al. |
| 8,883,712 | B2 | 11/2014 | Kohle et al. |
| 9,073,818 | B2 | 7/2015 | Herrwerth et al. |
| 2003/0127024 | A1* | 7/2003 | Heiberger ............... C04B 12/04 106/634 |
| 2004/0258651 | A1 | 12/2004 | Pascaly et al. |
| 2007/0231289 | A1 | 10/2007 | Gruning et al. |
| 2008/0108709 | A1 | 5/2008 | Meyer et al. |
| 2009/0170734 | A1 | 7/2009 | Schwab et al. |
| 2011/0048447 | A1* | 3/2011 | Muller .................... A61K 8/41 132/206 |
| 2011/0206623 | A1 | 8/2011 | Wenk et al. |
| 2013/0071343 | A1 | 3/2013 | Herrwerth et al. |
| 2013/0078208 | A1 | 3/2013 | Herrwerth et al. |
| 2013/0171087 | A1 | 7/2013 | Herrwerth et al. |
| 2014/0286889 | A1* | 9/2014 | Koehle ................. A61K 8/416 424/70.28 |
| 2015/0203443 | A1 | 7/2015 | Klostermann et al. |

FOREIGN PATENT DOCUMENTS

| CA | 2044234 | A1 | 12/1991 |
|---|---|---|---|
| CN | 1395600 | A | 2/2003 |
| CN | 102933543 | A | 2/2013 |
| DE | 2430140 | A1 | 6/1974 |
| DE | 3608093 | A1 | 9/1987 |
| DE | 3877422 | T2 | 4/1988 |

(Continued)

OTHER PUBLICATIONS

Bertin et al. (J Drugs Dermatol. Oct. 2011;10(10):1102-5) (Year: 2011).*
WO2012084336 (A2) (English Machine Translation). (Year: 2012).*
Schrader, K. et al., "Grundlagen und Rezepturen der Kosmetika" ["Principles and Formulations of Cosmetics"], 1989, 2nd edition, p. 329 to 341, Hüthig Buch Verlag Heidelberg.

(Continued)

*Primary Examiner* — Kortney L. Klinkel
*Assistant Examiner* — William Y Lee
(74) *Attorney, Agent, or Firm* — Scully Scott Murphy and Presser

(57) ABSTRACT

The invention relates to cosmetic formulations comprising specific ester quats based on isopropanolamine or tetrahydroxypropyl ethylenediamine, and to the use of these ester quats in cosmetics.

5 Claims, 2 Drawing Sheets

(56) References Cited

FOREIGN PATENT DOCUMENTS

| | | |
|---|---|---|
| DE | 4308794 C1 | 4/1994 |
| DE | 10327871 A1 | 1/2005 |
| DE | 102008001788 A1 | 11/2009 |
| EP | 0293955 A2 | 4/1988 |
| EP | 0461419 A1 | 12/1991 |
| EP | 0483195 | 5/1992 |
| EP | 0861938 A2 | 9/1998 |
| EP | 0835862 B1 | 3/2001 |
| EP | 1125574 A2 | 8/2001 |
| EP | 2168564 A2 | 3/2010 |
| EP | 2387986 A2 | 11/2011 |
| WO | WO9101295 | 2/1991 |
| WO | 9416677 A1 | 8/1994 |
| WO | WO2004112731 A2 | 12/2004 |
| WO | WO2006034992 A1 | 4/2006 |
| WO | WO2008092676 A1 | 8/2008 |
| WO | WO2009138306 A1 | 11/2009 |
| WO | 2011120822 A1 | 10/2011 |

OTHER PUBLICATIONS

Shapiro, I., et al., "Environmentally Friendly Ester Quats", Cosmetics and Toiletries Magazine, Dec. 1994, vol. 109, pp. 77-80.
Brock, M., et al., "Neue Entwicklungen auf dem Gebiet der Waescheweichspueler", Tens. Surf. Det., 30, pp. 394-399, 1993, English language abstract only.
Puchta, R., et al., "A New Generation of Softners", Tenside Surf. Det. 30, May 1993, 3, pp. 186-191.
Lagerman, R., et al. "Synthesis and Performance of Ester Quaternary Biodegradable Softners", JAOCS, Jan. 1994, pp. 97-100, vol. 71, No. 1.
Chinese Office Action dated Jan. 23, 2019 issued in Chinese Patent Application No. 201510795916.5, with English-language translation.

* cited by examiner

FORMULATION COMPRISING ESTER QUATS BASED ON ISOPROPANOLAMINE AND TETRAHYDROXYPROPYL ETHYLENEDIAMINE

FIELD OF THE INVENTION

The invention relates to cosmetic formulations comprising specific ester quats based on isopropanolamine or tetrahydroxypropyl ethylenediamine, and to the use of these ester quats in cosmetics.

BACKGROUND OF THE INVENTION

DE3608093 describes quaternary ammonium compounds comprising two 2-acyloxyalkyl groups, the acyl groups of which are derived from saturated or unsaturated carboxylic acids having 12 to 22 carbon atoms, including dimethyldi(oleoyl-oxyisopropyl)ammonium methosulphate, and the use of such substances in textile-softening formulations.

DE3877422 describes similar quaternary ammonium compounds, the corresponding acyl groups of which contain at most 17 carbon atoms, including dimethyldi(palmitoyl-oxyisopropyl)ammonium chloride, and the use of such substances in textile-softening formulations, but also mentions their suitability for hair conditioners.

Ester quats obtainable hitherto, which are suitable for use in hair conditioning, are solid substances which are only converted to a formulatable form by using solvents, as a result of which it is stipulated which solvent will be present in the end formulation. This limits the degrees of freedom of the formulation options.

SUMMARY OF THE INVENTION

The present invention provides a composition which exerts excellent conditioning effects on keratin fibres.

Surprisingly, it has been found by the Applicant of the present invention that the formulations described below are able to solve the problem addressed by the invention.

The present invention provides cosmetic formulations comprising 0.2 to 25% by weight, preferably 0.5 to 15% by weight, particularly 1 to 10% by weight, of at least one ester quat selected from
I) at least one compound of general formula I)

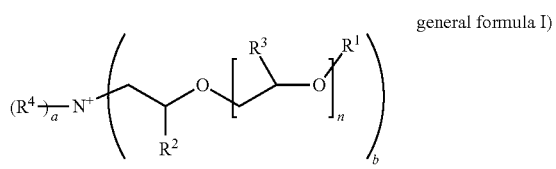

general formula I)

where $R^1$ is an acyl residue of an at least mono unsaturated fatty acid having a chain length of 18 to 24 carbon atoms or the acyl residue of isostearic acid or ricinoleic acid,
where $R^2$ is an alkyl residue having 1 to 6 carbon atoms, preferably methyl, ethyl, propyl or isopropyl, particularly preferably methyl,
where $R^3$ is an alkyl residue having 1 to 6 carbon atoms, or hydrogen, preferably methyl, ethyl, propyl or isopropyl, particularly preferably methyl or hydrogen,
where $R^4$ is an alkyl residue having 1 to 6 carbon atoms, or hydrogen, preferably methyl, ethyl, propyl or isopropyl, particularly preferably ethyl or methyl,
where n=0, 1, 2, 3, 4, 5, 6, 7, 8, 9, 10 to 20, and
where a=1 to 3 and b=1 to 3,
with the proviso that a+b=4,
and with the proviso that, if n=0, at least one $R^4$ is ethyl or propyl, preferably ethyl, and
II) at least one compound of the general formula II)

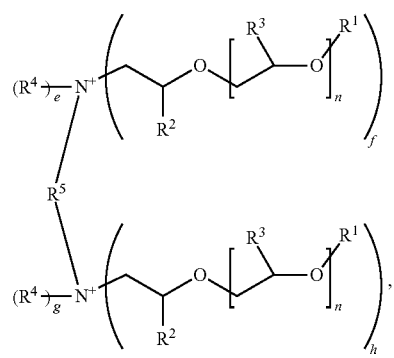

general formula II)

where $R^1$ is an acyl residue of an at least monounsaturated fatty acid having a chain length of 18 to 24 carbon atoms or the acyl residue of isostearic acid or ricinoleic acid, or hydrogen, with the proviso that at least one $R^1$ is not hydrogen,
where $R^2$ is an alkyl residue having 1 to 6 carbon atoms, preferably methyl, ethyl, propyl or isopropyl, particularly preferably methyl,
where $R^3$ is an alkyl residue having 1 to 6 carbon atoms, or hydrogen, preferably methyl, ethyl, propyl or isopropyl, particularly preferably methyl or hydrogen where $R^4$ is an alkyl residue having 1 to 6 carbon atoms, or hydrogen, preferably methyl, ethyl, propyl or isopropyl, particularly preferably methyl or ethyl,
where $R^5$ is a divalent, saturated or unsaturated, straight-chain, branched or cyclic, optionally substituted hydrocarbon residue which is optionally interrupted by oxygen or nitrogen atoms or carboxyl groups, preferably butylene, propylene, ethylene or methylene, particularly preferably butylene and ethylene, especially preferably ethylene,
where n=0, 1, 2, 3, 4, 5, 6, 7, 8, 9, 10 to 20 and
where e=1 to 2 and f=1 to 2, g=1 to 2 and h=1 to 2,
with the proviso that e+f=3 and g+h=3, and
40 to 99.8% by weight, preferably 50 to 99.5% by weight, particularly 60 to 99% by weight of water, wherein the percentages by weight refer to the overall formulation.

One advantage of the present invention is that the ester quats used are liquid at room temperature and can therefore easily be incorporated into a final consumer formulation without the use of solvents, as a result of which such a solvent does not necessarily have to be present in said formulation.

A further advantage of the present invention is that the shine of the treated keratin fibres is increased.

A further advantage of the present invention is that the compounds used develop a good effect even in small use amounts.

It is a further advantage that the compounds used have little impact from an ecological point of view.

It is a further advantage that the compounds used exhibit an improved conditioning effect on keratin fibres with longer rinse-off times than quaternary ester compounds known hitherto.

A further advantage of the present invention is that they have increased hydrolysis stability in the formulation.

A further advantage of the present invention is that they do not crystallize out.

A further advantage of the present invention is that they are effective in relatively low use concentrations.

A further advantage of the present invention is that they protect hair colorants from being washed out.

A further advantage of the present invention is that they protect keratin fibres against thermally induced damage.

A further advantage of the present invention is that they reduce the combing forces on wet and dry hair.

A further advantage of the present invention is that it is particularly economical.

A further advantage of the present invention is that it can be prepared methanol-free.

DETAILED DESCRIPTION OF THE INVENTION

Figure 1:
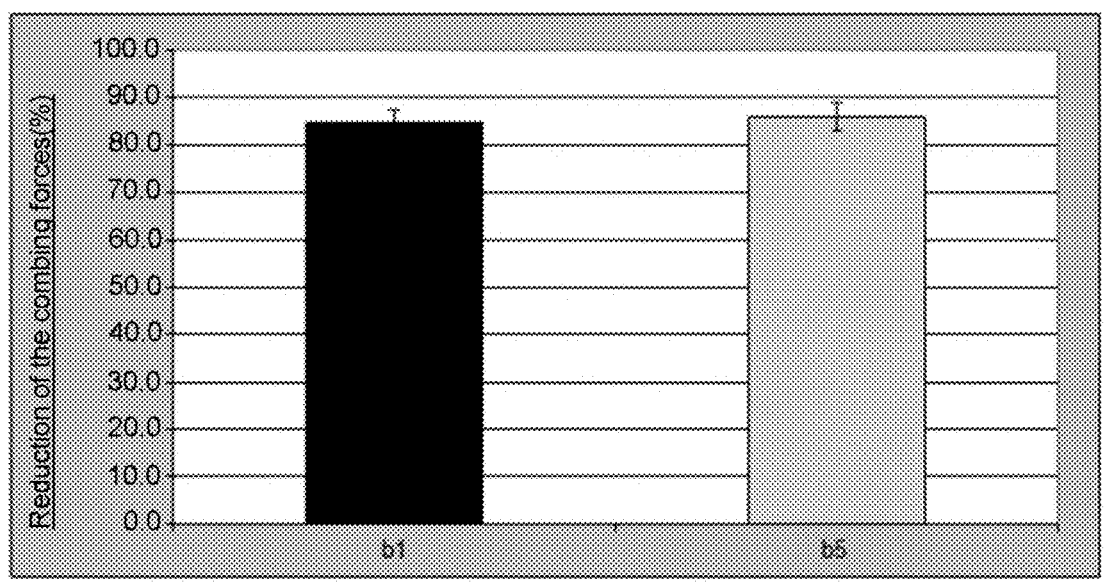
FIG. 1 is a comparison of the reduction of the combing forces during treatment of hair tresses using inventive formulations b1 and b5.

Unless otherwise stated, all percentages (%) given are percentages by weight.

The quaternized amine ester salts used in the context of the invention can be prepared by relevant methods of preparative organic chemistry. Usually, the preparation of ester quats is based on a multistage process in which the esterified alkanolamine is first prepared by reacting an alkanolamine with carboxylic acids or corresponding derivatives, and said alkanolamine is then subsequently quaternized with a suitable reagent. In connection with the present invention, the alkanolamine used is dimethylmono-, methyldi- or triisopropanolamine or mixtures thereof, in particular methyldiisopropanolamine.

In the context of suitable preparation processes, reference is made to EPO483195, according to which trialkanolamine is partially esterified in the presence of hypophosphorous acid with fatty acids, air is passed through and then quaternization is carried out with dimethyl sulphate or ethylene oxide. The compounds listed therein serve as plasticizers for textiles. DE4308794 describes the preparation of solid ester quats by carrying out the quaternization of the triethanolamine esters in the presence of suitable dispersants. Overviews of these topics can be found, for example, under R. Puchta et al. in Tens. Surf. Det., 30, 186 (1993), M. Brock in Tens. Surf. Det., 30, 394 (1993), R. Lagerman et al. in J. Am. Chem. Soc., 71, 97 (1994) or under I. Shapiro in Cosm. Toil., 109, 77 (1994).

If the formulation according to the invention comprises component I), it is preferable that said formulation additionally comprises in an amount of 0.001% by weight to 8% by weight, where the percentages by weight refer to the overall formulation:

Ia) at least one compound of general formula Ia)

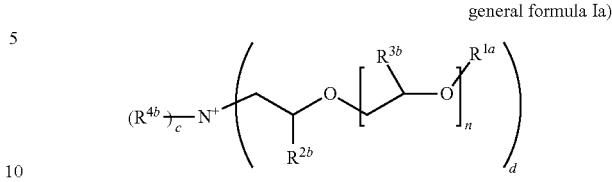

general formula Ia)

where $R^{1a}$ is an acyl residue of another carboxylic acid as defined for $R^1$, and
where $R^{2b}$ is an alkyl residue having 1 to 6 carbon atoms, preferably methyl, ethyl, propyl or isopropyl, particularly preferably methyl,
where $R^{3b}$ is an alkyl residue having 1 to 6 carbon atoms, or hydrogen, preferably methyl, ethyl, propyl or isopropyl, particularly preferably methyl or hydrogen,
where $R^{4b}$ is an alkyl residue having 1 to 6 carbon atoms, or hydrogen, preferably methyl, ethyl, propyl or isopropyl, particularly preferably methyl or ethyl,
where c=1 to 3, and d=1 to 3,
with the proviso that c+d=4.

In the formulation according to the invention, besides a compound of the general formula I), further compounds may therefore be present which, apart from the residue $R^1$, correspond to the compound of the general formula I), i.e., the analogous residue $R^{1a}$ is the acyl residue of another carboxylic acid, in particular of another fatty acid.

In this context, it is preferable that the compounds of the general formula I) constitute at least 30% by weight, preferably at least 50% by weight, particularly preferably at least 75% by weight, based on all of the compounds of the general formula I) and Ia) contained in the formulation.

The formulations therefore preferably comprise a mixture of at least one compound of the general formula I) and at least one compound of the general formula Ia), as arises, for example, when using technical-grade fatty acid cuts which have longer or shorter acyl residues than defined above for $R^1$.

Very particular preference is given to mixtures which are obtained if the mixture used is mixed plant oils with a carbon chain distribution for which the following applies:

| Chain length of $R^1$ or $R^{1a}$ (' = number of double bond(s)) | Proportion based on the overall mixture |
| --- | --- |
| <C 16 | 0-2% by weight |
| C 16 | 4-7% by weight |
| C 16' | 0-2% by weight |
| C 18' | 0-4% by weight |
| C 18' | 55-65% by weight |
| C 18" | 15-25% by weight |
| C 18''' | 6-12% by weight |
| >C 18 | 0-4% by weight |

Preferred formulations of this embodiment comprise compounds of general formula I) or Ia) where a=b=c=d=2.

This preferably applies also to the components I) and Ia): If b is >1, the residues $R^1$ can be identical or different. If a is >1, the residues $R^4$ can be identical or different. If d is >1, the residues $R^{1a}$ can be identical or different. If c is >1, the residues $R^{4b}$ can be identical or different. If n is >1, the residues $R^3$ can be identical or different.

Preferred formulations comprise at least one compound of general formula I) where a=b=2. A particularly preferred formulation according to the invention is characterized in that said formulation comprises at least one compound of the general formula I), where $R^1$ is the acyl residue of oleic acid and a=b=2.

Preferred components II are present in accordance with the invention which have a degree of esterification of 2-4, preferably a degree of esterification of 2.5-4 and particularly preferably of 2.8-3.9.

The term "degree of esterification" in connection with general formula II) of the present invention is understood to mean how many residues $R^1$ not equal to hydrogen are present per molecule of general formula II).

This preferably applies also to the components II): Preferably f=2 and h=2. If two or more residues $R^1$ are present in the molecule, the residues $R^1$ may be identical or different. Likewise, the residues $R^4$ may be identical or different. If n is >1, the residues $R^3$ can be identical or different.

This applies to both components I) and II). $R^1$ as acyl residue of an at least monounsaturated fatty acid with a chain length of 18 to 24 carbon atoms can contain one or more, for example two or three, double bonds.

Preferred formulations according to the invention are characterized in that $R^1$ as acyl residue of an at least monounsaturated fatty acid with a chain length of 18 to 24 carbon atoms is selected from the acyl residues of the acids selected from oleic acid, elaidic acid, vaccenic acid, gadoleic acid, icosenoic acid, cetoleic acid, erucic acid, nervonic acid, linolic acid, alpha-linolenic acid, gamma-linolenic acid, calendulic acid, punicic acid, alpha-elaeostearic acid, beta-elaeostearic acid, arachidonic acid, timnodonic acid, clupanodonic acid and cervonic acid, wherein oleic acid is particularly preferred. According to the invention, it is also possible to use mixtures of these carboxylic acids.

Preferred formulations according to the invention are characterized in that they comprise no fatty acids or fatty acid salts.

It has proven to be advantageous if the formulations according to the invention additionally comprise 0.5 to 20% by weight, preferably 1 to 10% by weight, in particular 2 to 7% by weight, of at least one fatty alcohol, where the percentages by weight refer to the total formulation.

Fatty alcohol in this context is preferably understood as meaning an unbranched or branched monoalcohol with an alkyl group of 8 to 30 carbon atoms, which may also be unsaturated. Preferred fatty alcohols are octanol, decanol, lauryl alcohol, isolauryl alcohol, anteisolauryl alcohol, myristyl alcohol, isomyristyl alcohol, cetyl alcohol, palmoleyl alcohol, stearyl alcohol, isostearyl alcohol, anteisostearyl alcohol, eicosanol, petroselinyl alcohol, Guerbet alcohol, arachyl alcohol, gadoleyl alcohol, behenyl alcohol, erucyl alcohol, hectacosanol, octacosanol, and melissyl alcohol, and mixtures thereof, in particular technical-grade mixtures, preferably technical-grade coconut or tallow fatty alcohols having 12 to 18, preferably having 16 to 18, carbon atoms, as well as the monounsaturated fatty alcohols, such as oleyl alcohol, elaidyl alcohol, delta-9-cis-hexadecenol, delta-9-octadecenol, trans-delta-9-octadecenol, cis-delta-11-octadecenol, trans-10,cis-12-hexadecadien-1-ol, octacosa-10,19-dien-1-ol and polyunsaturated fatty alcohols such as e.g. linoleyl alcohol (9Z,12Z-octadecadien-1-ol), elaidolinoleyl alcohol (9E,12E-octadecadien-1-ol), linolenyl alcohol (9Z, 12Z,15Z-octadecatrien-1-ol), elaidolinolenyl alcohol (9E, 12E,15-E-octadecatrien-1-ol), with mixtures of coconut or tallow fatty alcohols having 16 to 18 carbon atoms being particularly preferred.

Mixtures of fatty alcohols according to the invention may be used. It has been found to be advantageous and, is therefore preferred in accordance with the invention, if mixtures of fatty alcohols are used which comprise 80% by weight to 97% by weight of at least one linear, saturated fatty alcohol and 3% by weight to 20% by weight of at least one at least monounsaturated or branched fatty alcohol, such as, for example, isostearyl alcohol or guerbet alcohols, wherein the percentage refers to the overall fatty alcohol content. In this context, the mixtures preferably comprise at least one C14 to C20 fatty alcohol, and in particular oleyl alcohol or isostearyl alcohol, as saturated fatty alcohol. The proportion of unsaturated or branched fatty alcohols has a positive effect on the viscosity, texture, colour and stability of the formulations according to the invention. It is particularly preferred in this context, if the unsaturated or branched fatty alcohol in the mixture is identical to the alcohol resulting from the acyl residue $R^1$ of general formula I) in the formulation, in which the acid group of the acid of the acyl residue $R^1$ has been reduced to the alcohol (e.g. $R^1$=acyl residue of oleic acid-->unsaturated alcohol in the mixture oleyl alcohol).

It has proven to be advantageous if the formulations according to the invention additionally comprise 0.1 to 10% by weight, preferably 0.25 to 5% by weight, in particular 0.5 to 2.5% by weight, of at least one emulsifier, where the percentages by weight refer to the total formulation.

Emulsifiers preferred in this context are selected from the group of fatty alcohol alkoxylates, in particular the fatty alcohol ethoxylates. Particularly preferred fatty alcohol ethoxylates present are selected from polyoxyethylene ethers of lauryl alcohol, CAS number 9002-92-0, macrogol lauryl ether, e.g., polyoxyethylene (4) lauryl ether (Laureth-4, INCI), polyoxyethylene (9) lauryl ether Laureth-9 (INCI), polyoxyethylene (23) lauryl ether Laureth-23 (INCI), polyoxyethylene ethers of cetyl alcohol, CAS number 9004-95-9, e.g., polyoxyethylene (2) cetyl ether Ceteth-2 (INCI), polyoxyethylene (10) cetyl ether Ceteth-10 (INCI), polyoxyethylene (20) cetyl ether Ceteth-20 (INCI), polyoxyethylene ethers of cetylstearyl alcohol, CAS number 68439-49-6, e.g., polyoxyethylene (6) cetylstearyl ether Ceteareth-6 (INCI), polyoxyethylene (20) cetylstearyl ether Ceteareth-20 (INCI), polyoxyethylene (25) cetylstearyl ether Ceteareth-25 (INCI), polyoxyethylene ethers of stearyl alcohol, CAS number 9005-00-9, e.g., polyoxyethylene (2) stearyl ether Steareth-2 (INCI), polyoxyethylene (10) stearyl ether Steareth-10 (INCI), polyoxyethylene (20) stearyl ether Steareth-20 (INCI), polyoxyethylene ethers of oleyl alcohol, CAS number 9004-98-2, e.g., polyoxyethylene (2) oleyl ether Oleth-2 (INCI), polyoxyethylene (10) oleyl ether Oleth-10 (INCI), polyoxyethylene (20) oleyl ether Oleth-20 (INCI), or polyoxyethylene (10) tridecyl ether (CAS number 24938-91-8) and Trideceth-10 (INCI).

Alternatively preferred emulsifiers are selected from the group of polyol esters, in particular, the glycerol esters and polyglycerol esters, in particular, the polyglycerol esters. Preferably present (poly)glycerol esters are characterized in that they are partial esters. Particularly preferred polyglycerol partial esters are selected from polyglycerol partial esters as described in EP-B-0 835 862, which are obtainable by esterification of a polyglycerol mixture with a degree of esterification of the polyglycerol between 30 and 75% and saturated or unsaturated, linear or branched fatty acids with 12 to 22 carbon atoms and dimer fatty acids with an average functionality of 2 to 2.4, esters of citric acid such as, for example, the O/W emulsifier glyceryl stearate citrate, (2-hydroxy-1,2,3-propanetricarboxylic acid-1,2,3-propanetriol monooctadecanoate, INCI Glyceryl Stearate Citrate, CAS 39175-72-9), the citric acid ester of glyceryl stearate, commercially available inter alia under the name AXOL C 62, glyceryl stearate citrate as described in WO2006034992 and WO2008092676 and glyceryl oleate citrate as described in WO2004112731, likewise simple polyglycerol esters, such as, for example, polyglycerol-3 distearate, polyglyceryl-10 stearate, polyglyceryl-6 distearate, mixed esters of polyglycerol and methyl glucose and stearic acid, such as, for example, polyglyceryl-3 methyl glucose distearate and (poly)glycerol partial esters with one or more carboxylic acids having 10 to 24 carbon atoms and residues of a polyfunctional carboxylic acid.

In principle, sorbitan or sucrose esters can also be used as polyol esters. A customary combination is, for example, Sorbitan Stearate & Sucrose Cocoate.

Emulsifiers preferably present in a further alternative are selected from the group of modified siloxanes, for example, those which also carry polyethers besides aliphatic groups based on alpha-olefins. Siloxane-based emulsifiers for oil-in-water emulsions must have a hydrophilic character, for which reason they are generally pure polyether siloxanes. Particularly suitable examples are relatively hydrophobic polyether siloxanes as described in EP1125574, high molecular weight polyether siloxanes as described in EP2168564 and organomodified siloxane block copolymers as described in WO2009138306. Preferably present modified siloxanes are characterized in that they have a HLB value >8. Particularly preferred modified siloxanes are selected from the Bis-PEG/PPG-16/16 Dimethicone, PEG/PPG-16/16 Dimethicone, Bis-PEG/PPG-20/5 PEG/PPG-20/5 Dimethicone and Methoxy PEG/PPG-25/4 Dimethicone.

In connection with the present invention, the aforementioned emulsifiers produce particularly storage-stable formulations.

Particular preference is given to formulations according to the invention comprising a compound of general formula I) where $R^1$ is an acyl residue of isostearic acid,
where $R^2$ is an alkyl residue having 1 to 6 carbon atoms, preferably methyl, ethyl, propyl or isopropyl, particularly preferably methyl,
where $R^3$ is an alkyl residue having 1 to 6 carbon atoms, or hydrogen, preferably methyl, ethyl, propyl or isopropyl, particularly preferably methyl or hydrogen,
where $R^4$ is an alkyl residue having 1 to 6 carbon atoms, or hydrogen, preferably methyl, ethyl, propyl or isopropyl, particularly preferably methyl or ethyl,
where n=0, 1, 2, 3, 4, 5, 6, 7, 8, 9, 10 to 20, and
where a=1 to 3 and b=1 to 3, with the proviso that a+b=4, and with the proviso that, if n=0, at least one $R^4$ is ethyl or propyl, preferably ethyl,
and at least one emulsifier is selected from the group of: ethoxylated emulsifiers, such as, e.g., TEGINACID (Glyceryl Stearate, Ceteareth-20) or TEGINACID C (Ceteareth-25), or TEGO Acid S 40 P (PEG-40 Stearate) or TEGO Alkanol IC 20 (Isoceteth-20) or Laureth-23 or Steareth-20 or Steareth-21 or TEGO Care 165 (Glyceryl Stearate, PEG-100 Stearate) or TEGO Care 215 (Ceteareth-15, Glyceryl Stearate), organomodified siloxanes, such as, e.g., ABIL Care 85 (Bis-PEG/PPG-16/16 PEG/PPG-16/16 Dimethicone; Caprylic/Capric Triglyceride) or ABIL Care XL 80 (Bis-PEG/PPG-20/5 PEG/PPG-20/5 Dimethicone; Methoxy PEG/PPG-25/4 Dimethicone; Caprylic/Capric Triglyceride), cationic surfactants, such as, e.g., VARISOFT PATC (Palmamidopropyltrimonium Chloride) or VARISOFT TA 100 (Distearyldimonium Chloride) or VARISOFT BT 85 (Behentrimonium Chloride), sugar-based emulsifiers, such as, e.g., TEGO Care PS (Methyl Glucose Sesquistearate) or TEGO Care CG 90 (Ceteary Glucoside), glycerol-based emulsifiers, such as e.g. AXOL C62 Pellets (Glyceryl Stearate Citrate) or TEGO Care PL 4 (Polyglyceryl-4 Laurate), TEGO Care PSC 3 (Polyglyceryl-3 Stearate/Citrate), sugar and glycerol-based emulsifiers, such as, e.g., TEGO Care 450 (Polyglyceryl-3 Methylglucose Distearate) or TEGO Care PS (Methyl Glucose Sesquistearate) and mixtures of the above, such as, e.g., TEGO Care LTP (Sorbitan Laurate, Polyglyceryl-4 Laurate, Dilauryl Citrate).

The formulation according to the invention may additionally comprise III) at least one compound of general formula III)

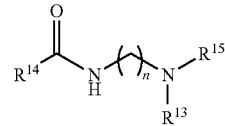

general formula III)

where
$R^{14}$—CO is selected from an aliphatic, linear or branched acyl residue having 6 to 22 carbon atoms comprising 0, 1, 2 or 3 double bonds, which generally stems from a naturally occurring or synthetically prepared fatty acid,
$R^{15}$ and $R^{13}$ are selected from identical or different alkyl residues, which can optionally carry functional groups such as hydroxy groups, ester groups, amines, amides or other polar substituents, preference being given to unsubstituted hydrocarbon residues which have at most one or more branches, particular preference being given to hydrocarbon residues having 1 to 6 carbon atoms, with ethyl and methyl residues being very particularly preferred according to the invention.
n=a whole number selected from 1 to 10, preferably from 2 to 7, particularly from 2 to 4.

The compounds of general formula III are usually prepared by amidation of natural or synthetic fatty acids and fatty acid cuts with dialkylaminoamines. Typical examples of such fatty acids are caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaeostearic acid, arachic acid, gadoleic acid, behenic acid and erucic acid, and technical-grade mixtures thereof which are produced. e.g. during the pressurized cleavage of natural fats and oils, during the reduction of aldehydes from the Roelen oxo synthesis or the dimerization of unsaturated fatty acids. Particular preference is usually given to the fatty acid cuts which are obtainable from coconut oil or palm oil, with the use of stearic acid generally being particularly preferred.

Depending on the intended use, the formulation according to the invention may comprise the compounds of general formula I), II), III) and optionally Ia) in various ratios. In the formulation according to the invention, components I) or II) are preferably present in total with respect to component III) in a weight ratio of 20:1 to 1:20, particularly 10 to 1 to 1 to 10. Depending on the desired effect, the weight ratio can also be varied from 5:1 to 1:5 or from 3:1 to 1:3.

The formulations according to the invention can comprise, e.g., at least one further additional component selected from
emollients,
coemulsifiers,
thickeners/viscosity regulators/stabilizers,
antioxidants, hydrotropes (or polyols),
solids and fillers,
pearlescence additives,
deodorant and antiperspirant active ingredients,
insect repellents,
self-tanning agents,
preservatives,
conditioners,
perfumes,
dyes,
cosmetic active ingredients,
care additives,
superfatting agents, and
solvents.

Substances which can be used as exemplary representatives of the individual groups are known to the person skilled in the art and can be found for example in the German application DE 102008001788.4. This patent application is herewith incorporated as reference and thus forms part of the disclosure.

As regards further optional components and the amounts of these components used, reference is made expressly to the relevant handbooks known to the person skilled in the art, e.g., K. Schrader, "Grundlagen and Rezepturen der Kosmetika [Fundamentals and Formulations of Cosmetics]", 2nd edition, pages 329 to 341, Htithig Buch Verlag Heidelberg.

The amounts of the particular additives are governed by the intended use.

Typical guide formulations for the respective applications are known prior art and are contained, for example, in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

Formulations preferred according to the invention, in particular those for treating keratin fibres, in particular human hair, comprise, optionally, in total 0.1 to 7% by weight, preferably 0.2 to 5% by weight and particularly preferably 0.3 to 3% by weight, of compounds of general formula I) and optionally Ia) or formula II) and, optionally, additionally 0.1 to 7% by weight, preferably 0.2 to 5% by weight and particularly preferably 0.3 to 3% by weight, of compounds of general formula III), where the percentages by weight refer to the total formulation.

Particularly good results can be achieved at the predefined concentrations of 0.2 to 3% by weight. The application of the formulations according to the invention to keratin fibres, in particular to human hair, however, is not limited to the use of the active ingredients in low concentration. It is likewise possible to use concentrated formulations according to the invention in which the predefined concentrations are 2 to 20% by weight or 3 to 14% by weight, in particular 5 to 12% by weight.

It is preferred according to the invention if the formulation has a pH from 3.0 to 5.5, preferably 3.5 to 5.0.

The charge of the compounds of formulae I) or II) present in the formulation according to the invention must be compensated by corresponding anions; this takes place by means of counteranions present in the formulation according to the invention.

Such counteranions are, for example, the halides, pseudohalides, anions of mineral acids, sulphates, sulphites, hydrogensulphites, sulphonate, alkyl- and arylsulphonates, phosphate, hydrogenphosphates, phosphites, hydrogenphosphites, phosphonites, carboxylates, borates, carbonates, sulphides, hydrogensulphides, lactate, glycolate, formate, acetate or propionate.

These anions are preferably selected from those which are suitable for cosmetic application and are therefore for example nontoxic. Particularly preferably, at least one counteranion to the compound of general formula I) or II) selected from chloride, bromide, iodide, alkyl sulphate, e.g. methyl sulphate, ethyl sulphate, alkylsulphonate, e.g., methylsulphonate, triflate, tosylate, phosphate, sulphate, hydrogensulphate, lactate, glycolate, acetate and citrate, preferably chloride, methyl sulphate, and ethyl sulphate, particularly preferably methyl sulphate and ethyl sulphate is present.

The invention further provides a compound of general formula I)

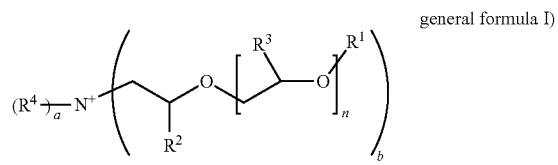

general formula I)

where $R^1$ is an acyl residue of isostearic acid,
where $R^2$ is an alkyl residue having 1 to 6 carbon atoms, preferably methyl, ethyl, propyl or isopropyl, particularly preferably methyl,
where $R^3$ is an alkyl residue having 1 to 6 carbon atoms, or hydrogen, preferably methyl, ethyl, propyl or isopropyl, particularly preferably methyl or hydrogen,
where $R^4$ is an alkyl residue having 1 to 6 carbon atoms, or hydrogen, preferably methyl, ethyl, propyl or isopropyl, particularly preferably methyl or ethyl,
where n=0, 1, 2, 3, 4, 5, 6, 7, 8, 9, 10 to 20, and
where a=1 to 3, and b=1 to 3
with the proviso that a+b=4,
and with the proviso that, if n=0, at least one $R^4$ is ethyl or propyl, preferably ethyl.

Compounds of general formula I) preferred according to the invention are those where a=b=2, particularly preferably where $R^2$=methyl.

The invention further provides compounds of general formula II)

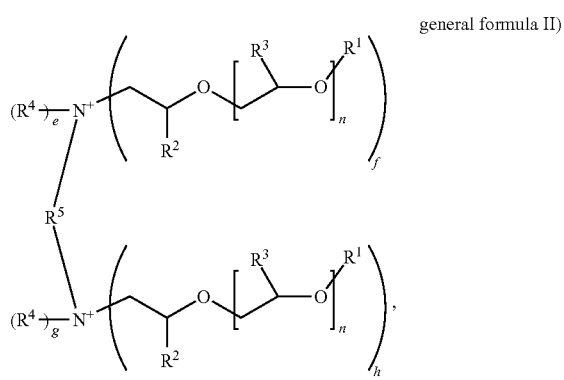

general formula II)

where $R^1$ is an acyl residue of an at least monounsaturated fatty acid having a chain length of 18 to 24 carbon atoms or the acyl residue of isostearic acid or ricinoleic acid, or hydrogen, with the proviso that at least one $R^1$ is not hydrogen,
where $R^2$ is an alkyl residue having 1 to 6 carbon atoms, preferably methyl, ethyl, propyl or isopropyl, particularly preferably methyl,
where $R^3$ is an alkyl residue having 1 to 6 carbon atoms, or hydrogen, preferably methyl, ethyl, propyl or isopropyl, particularly preferably methyl or hydrogen,
where $R^4$ is an alkyl residue having 1 to 6 carbon atoms, or hydrogen, preferably methyl, ethyl, propyl or isopropyl, particularly preferably methyl or ethyl,
where $R^5$ is a divalent, saturated or unsaturated, straight-chain, branched or cyclic, optionally substituted hydrocarbon residue which is optionally interrupted by oxygen or nitrogen atoms or carboxyl groups, preferably butylene, propylene, ethylene or methylene, particularly preferably butylene and ethylene, especially preferably ethylene,
where n=0, 1, 2, 3, 4, 5, 6, 7, 8, 9, 10 to 20 and where e=1 to 2 and f=1 to 2, g=1 to 2 and h=1 to 2,
with the proviso that e+f=3 and g+h=3.

Preferred compounds of general formula II) in accordance with the invention are those which have a degree of esterification of 2 to 4, preferably a degree of esterification of 2.5-4 and particularly preferably of 2.8 to 3.9.

This preferably applies also to the components II): Preferably f=2 and h=2. If two or more residues $R^1$ are present in the molecule, the residues $R^1$ may be identical or different. Likewise, the residues $R^4$ may be identical or different. If n is >1, the residues $R^3$ can be identical or different.

The above applies to $R^1$ for said components I) and II) present in the formulations according to the invention.

The compounds of general formulae I) and II) according to the invention and also compounds of general formulae I) and II) which are present in the formulations according to the invention, and also the formulations according to the invention, can be used in accordance with the invention for the treatment of keratin fibres, particularly for hair treatment.

In this connection, preference is given to using those compounds of general formula I) and II) which are described above as preferably being present in the formulations according to the invention.

The use according to the invention leads to the improvement in the conditioning, shine, flexibility, elasticity and/or combability, and also to a reduction in the probability of breakage of the treated fibres and, moreover, it reduces the antistatic forces between the fibres.

The use according to the invention leads to the protection of the fibres against heat.

The present invention is described in exemplary fashion in the examples cited below, without the invention, the scope of application of which results from the whole of the description and the claims, being limited to the embodiments mentioned in the examples.

EXAMPLES

Synthesis Example 1

Preparation of "1-Propanaminium, 2-Hydroxy-N-(2-Hydroxypropyl)-N-Ethyl-N-Methyl, Diester with Mixed Plant Oil Fatty Acid, Ethyl Sulphate" (According to the Invention)

560 g (2 mol) of mixed plant oil fatty acid were mixed with 150 g (1.02 mol) of methyldiisopropanolamine and heated to 180° C. with stirring. Water of reaction was distilled off continuously. After the majority of water of reaction had been distilled at atmospheric pressure, vacuum was applied and the acid number of the reaction mixture was reacted down to <7 mg KOH/g. The resulting ester amine was cooled to 60° C. and admixed in portions with 146 g (0.95 mol) of diethyl sulphate, such that the reaction temperature did not exceed 100° C.

After cooling to room temperature, the total amine number (TAN) and the active content of the finished product were analysed.

TAN=5.0 mg KOH/g; active content 1.25 meq/g (cationic active content according to Epton).

Example 2

Preparation of "1-Propanaminium, 2-Hydroxy-N-(2-Hydroxypropyl)-N,N-Dimethyl, Diester with Palm Fatty Acid, Methyl Sulphate" (not According to the Invention)

1020 g (4 mol) of palmitic acid (technical-grade quality, approx. 98% pure) were admixed with 302 g (2.05 mol) of methyldiisopropanolamine and esterified as described in Example 1. The ester amine had an acid number of 5.6 mg KOH/g. This mixture was alkylated with 240 g (1.90 mol) of dimethyl sulphate as described in Example 1.

The TAN of the finished product was determined with 4.8 mg KOH/g, the active content was 1.33 meq/g.

Synthesis Example 3a

N,N,N',N'-Tetrakis (2-Hydroxypropyl)Ethylenediaminium, Tetraester with Plant Mixed Oil Fatty Acid, Methyl Sulphate (According to the Invention)

910.7 g (3.24 mol) of plant mixed oil fatty acid were mixed with 249.4 g (0.85 mol) of N,N,N',N'-tetrakis (2-hydroxypropyl)ethylenediamine and heated to 180° C. with stirring. Water of reaction was distilled off continuously. After the majority of water of reaction had been distilled at atmospheric pressure, vacuum was applied and the acid number of the reaction mixture was reacted down to <7 mg KOH/g. The resulting ester amine was cooled to 60° C. and admixed in portions with 107.2 g (0.85 mol) of dimethyl sulphate, such that the reaction temperature was maintained in the range of 60-90° C. After cooling to room temperature, the total amine number (TAN) and the active content of the finished product were analysed.

TAN=40.1 mg KOH/g; active content 0.71 meq/g (cationic active content according to Epton).

Synthesis Example 3b

N,N,N',N'-Tetrakis (2-Hydroxypropyl)Ethylenediaminium, Triester with Plant Mixed Oil Fatty Acid, Methyl Sulphate (According to the Invention)

843 g (3.0 mol) of plant mixed oil fatty acid were mixed with 292.4 g (1.0 mol) of N,N,N',N'-tetrakis (2-hydroxypropyl)ethylenediamine (Neutrol TE) and heated to 180° C. with stirring. Water of reaction was distilled off continuously. After the majority of water of reaction had been distilled at atmospheric pressure, vacuum was applied and the acid number of the reaction mixture was reacted down to <7 mg KOH/g. The resulting ester amine was cooled to 60° C. and admixed in portions with 189 g (1.5 mol) of dimethyl sulphate, such that the reaction temperature was maintained in the range of 60-90° C. After cooling to room temperature, the TAN and the active content of the finished product were analysed.

TAN=20.8 mg KOH/g; active content 0.95 meq/g (cationic active content according to Epton).

Example 4

Application Technology of Hair Treatment Compositions Using Example 1, Example 3 and Example 2 as Well as Commercial Market Products For the applications-related assessment, hair tresses were used which had been predamaged in a standardized manner by means of a bleaching treatment. For this purpose, standard hairdressing products were used. The damage to the hair tresses is described in detail in DE10327871.

For the applications-related assessment, the compound according to the invention from Example 1 was used in a simple cosmetic formulation.

The reference compounds used were the commercially available alkyl quat (INCI) Behentrimonium Chloride (VARISOFT® BT 85 Pellets, Evonik Industries) and the commercially available ester quat (INCI) DistearoylethylDimonium Chloride (VARISOFT® EQ 65 Pellets, Evonik Industries), as well as the compound dimethyldi(palmitoyloxyisopropyl)ammonium chloride.

The application properties upon use in hair rinses were tested in the following formulations (Table 1):

TABLE 1

| Hair rinse formulation for testing the hair conditioning properties | | | | | | | |
|---|---|---|---|---|---|---|---|
| Formulation Examples | C0a | 1a | V2a | V3a | V4a | 5a | 6a |
| TEGINACID® C, Evonik Industries (INCI: Ceteareth-25) | 0.5% | 0.5% | 0.5% | 0.5% | 0.5% | 0.5% | 0.5% |
| TEGO® Alkanol 1618, Evonik Industries (INCI: Cetearyl alcohol) | 5% | 5% | 5% | 5% | 5% | 5% | 5% |
| Synthesis Example 1 (100%) | | 1.5% | | | | | |
| Synthesis Example 2 (80% in isopropanol) | | | 1.9% | | | | |
| Synthesis Example 3a | | | | | | 1.5% | |
| Synthesis Example 3b | | | | | | | 1.5% |
| VARISOFT® EQ 65 Pellets (65% strength in C16 fatty alcohol), Evonik Industries (INCI: Distearoylethyl Dimonium Chloride, Cetearyl Alcohol) | | | | 2.3% | | | |
| VARISOFT® BT 85, (85% strength in isopropanol), Evonik Industries (INCI: Behentrimonium Chloride) | | | | | 1.76% | | |
| Water, demineralized | | | | to 100.0 | | | |
| Citric acid | | | | to pH 4.0 | | | |

The composition of the test formulations was deliberately chosen to be simple in order to avoid the test results being influenced by (normally present) formulation constituents. Besides the specified ingredients and/or instead of the specified ingredients, formulations according to the invention can also comprise further ingredients. In particular, the combination with further ingredients can lead to a synergistic improvement in the case of the described effects.

The hair was pretreated with a shampoo formulation (Table 2), which contains no conditioner.

TABLE 2

| Shampoo formulation for the pretreatment of the hair tresses. | |
|---|---|
| Texapon NSO ®, 28% strength, Cognis (INCI: Sodium Laureth Sulphate) | 42.9% |
| NaCl | 3% |
| Water, demineralized | to 100.0 |

Standardized Treatment of Predamaged Hair Tresses with Conditioning Samples:

The hair tresses predamaged as described above were washed with the shampoo formulation from Table 2.

Here, the hair tresses were wetted under running warm water. The excess water was gently squeezed out by hand, then the shampoo was applied and worked gently into the hair for 1 min (0.5 ml/2 g hair tress). The hair tress was rinsed for 30 s under running warm water. This procedure was repeated once more except that final rinsing was for 1 min.

Then, directly after washing, the hair tresses were conditioned with the hair rinse formulations from Table 1.

Here, the rinse was applied and gently worked into the hair (0.5 ml/2 g hair tress). After a residence time of 1 min, the hair was rinsed for a) 1 min or for b) 3 min.

Before the sensory assessment, the hair was dried for at least 12 h in the air at 50% humidity and 25° C.

Assessment Criteria:

The sensory evaluations were made using grades awarded on a scale from 1 to 5, with 1 being the worst evaluation and 5 being the best evaluation. The individual test criteria each contained their own evaluation.

The Test Criteria were:

Wet combability, wet feel, dry combability, dry feel, appearance/shine.

The tables below compare the results of the sensory assessment of the treatment of the hair tresses carried out as described above with a) 1 min rinsing time and for b) 3 min rinsing time with the formulation 1a according to the invention, the comparative formulations V2a, V3a and V4a and the control formulation C0a (control without test substance), and for aa) 1 min rinsing time and for bb) 3 min rinsing time with the formulation 7a according to the invention, the comparative formulations V2a, V3a and V4a and the control formulation C0a (control without test substance).

a) 1 Min Rinsing Time

TABLE 3a

Results of the conditioning of hair with 1 min rinsing time

|  | Wet combability | Wet feel | Dry combability | Dry feel |
|---|---|---|---|---|
| Inventive Formulation 1a | 5 | 5 | 5 | 5 |
| Comparative formulation 2a | 3.5 | 3 | 3.5 | 3.5 |
| Comparative formulation 3a | 3.5 | 3.5 | 4 | 3.5 |
| Comparative formulation 4a | 4.0 | 4.5 | 4.5 | 4.5 |
| Control C0a | 2 | 2 | 3 | 2.5 | b) 3 Min Rinsing Time

TABLE 3b

Results of the conditioning of hair with 3 min rinsing time

|  | Wet combability | Wet feel | Dry combability | Dry feel |
|---|---|---|---|---|
| Inventive Formulation 1a | 5 | 5 | 5 | 5 |
| Comparative formulation 2a | 3 | 3 | 3.5 | 3.5 |
| Comparative formulation 3a | 3 | 3 | 3.5 | 3 |
| Comparative formulation 4a | 4 | 4 | 4 | 4 |
| Control C0a | 2 | 2 | 3 | 2.5 |

The results in Table 3a show that the formulation 1a according to the invention has very good conditioning properties with 1 min rinsing time which are significantly superior to the comparative formulations V2a, V3a and V4a.

The results in Table 3b show that the formulation 1a according to the invention has even more markedly improved conditioning properties with 3 min rinsing time than after 1 min than the comparative formulations V2a, V3a and V4a. The comparative formulation V4a comprises, as conditioning compound, VARISOFT®BT 85 (85% strength in isopropanol, Evonik Industries, INCI: Behentrimonium Chloride), an alkyl quat which is known for its very good conditioning properties even in the case of long rinsing times. The comparative formulation V3a comprises, as conditioning compound, VARISOFT® EQ 65Pellets (65% strength in C 16 fatty alcohol, Evonik Industries, INCI: Distearoylethyl Dimonium Chloride, Cetearyl Alcohol), an ester quat, which has very good conditioning properties with 1 min rinsing time (see Table 3a), but shows distinctly poorer conditioning with 3 min rinsing time.

aa) 1 Min Rinsing Time

TABLE 3c

Results of the conditioning of hair with 1 min rinsing time

|  | Wet combability | Wet feel | Dry combability | Dry feel |
|---|---|---|---|---|
| Inventive Formulation 5a | 4.5 | 4.5 | 5 | 5 |
| Comparative formulation 2a | 3 | 3 | 3.5 | 3.5 |
| Comparative formulation 3a | 3.5 | 3.5 | 4 | 4 |
| Comparative formulation 4a | 4 | 4 | 4.5 | 4.5 |
| Control C0a | 2 | 2 | 3 | 2.5 |

Bb) 3 Min Rinsing Time

TABLE 3d

Results of the conditioning of hair with 3 min rinsing time

|  | Wet combability | Wet feel | Dry combability | Dry feel |
|---|---|---|---|---|
| Inventive Formulation 5a | 4.5 | 4 | 4.5 | 4.5 |
| Comparative formulation 2a | 3.0 | 3.0 | 3.5 | 3.0 |
| Comparative formulation 3a | 3.0 | 3.0 | 3.5 | 3.5 |
| Comparative formulation 4a | 4 | 4 | 4 | 4 |
| Control C0a | 2 | 2 | 3 | 2.5 |

The results in Table 3c show that the formulation 5a according to the invention has very good conditioning properties with 1 min rinsing time which are significantly superior to the comparative formulations V2a, V3a and V4a.

The results in Table 3d show that the formulation 5a according to the invention has even more markedly improved conditioning properties with 3 min rinsing time than after 1 min than the comparative formulations V2a, V3a and V4a. The comparative formulation V4a comprises, as conditioning compound, VARISOFT®BT 85 (85% strength in isopropanol, Evonik Industries, INCI: Behentrimonium Chloride), an alkyl quat which is known for its very good conditioning properties even in the case of long rinsing times. The comparative formulation V3a comprises, as conditioning compound, VARISOFT® EQ 65 Pellets (65% strength in C 16 fatty alcohol, Evonik Industries, INCI: Distearoylethyl Dimonium Chloride, Cetearyl Alcohol), an ester quat, which has very good conditioning properties with 1 min rinsing time (see Table 3c), but shows distinctly poorer conditioning with 3 min rinsing time.

Example 5

Influence of the Compounds According to the Invention on Combing Forces of Hair

Experimental Conditions:
Instrument: Diastron MTT 175
Measurement distance: 20 cm
Combing rate: 2000 mm/min
Hair tresses used: length=23 cm; width=1.5 cm; weight=2 g
Measurement conditions: T=22° C.

The hair tresses were measured with a residual moisture of 60%, determined by weight determination.

European, undamaged, dark brown hair was used for the experiments. To carry out the combing force measurements, this hair was damaged by means of perming in the laboratory in accordance with standard conditions:

1.) 4 g perming solution/g of hair, leave to act for 15 min, rinse out for 2 min under running tap water (T=35° C.). (Perming solution: Universal perming, Basler)

2.) 4 g of neutralizer (1 part neutralizing solution+3 parts water)/g of hair, allow to act for 10 min, rinse out for 2 min. (Neutralizing solution: foam neutralizer concentrate, Basler)

Carrying out the combing force measurement before the treatment with the test formulation:

The predamaged hair tresses were climatized overnight.

3.) The hair tress was dipped for 1 min in a buffer solution (Na citrate, pH=6).

4.) The hair tress was precombed by hand until no change in combing resistance was ascertained.

5.) The hair tress was clamped in the instrument and the first combing force measurement was carried out. The measurement was repeated a total of 10 times.

Treatment of the Tresses:

0.5 g of the respective test formulation was used per hair tress (2 g hair/0.5 g solution). The formulation was massaged into the hair for 30 sec and then left on for 5 min, then rinsed off under running tap water for 1 min or 3 min.

Carrying Out the Combing Force Measurement after Treatment with the Test Formulation:

Points 3-5 were repeated.

The combability (%) was then calculated before and after treatment with the test formulation.

Test Formulations Used:

The combing forces when used in hair rinses were tested in the following formulations (Table 4):

The results of the combing force measurements of the experiments carried out as described above with a) 1 min rinsing time and with b) 3 min rinsing time are compared with the formulation 1b according to the invention, the comparative formulations V3b and V4b and the control formulation C0b (control without test substance).

The results show that the formulation 1b according to the invention with 1 min rinsing time has a more marked reduction in the combing forces than the comparative formulations V3b. The results further show that the formulation 1b according to the invention with 3 min rinsing time has a more marked reduction in the combing forces than the comparative formulation V3b. The comparative formulation V3b comprises, as conditioning compound, VARISOFT® EQ 65 Pellets (65% strength in C 1618 fatty alcohol, Evonik Industries, INCI: Distearoylethyl Dimonium Chloride, Cetearyl Alcohol), an ester quat.

The results further show that the formulation 6b according to the invention with 3 min rinsing time has a more marked reduction in the combing forces than the comparative formulation V3b.

The comparative formulation V3b comprises, as conditioning compound, VARISOFT® EQ 65 Pellets (65% strength in C 1618 fatty alcohol, Evonik Industries, INCI: Distearoylethyl Dimonium Chloride, Cetearyl Alcohol), an ester quat.

The results also show that the formulation 5b according to the invention with 3 min rinsing time has a more marked reduction in the combing forces than the comparative formulations V3b and V4b.

The comparative formulation V3b comprises, as conditioning compound, VARISOFT® EQ 65 Pellets (65% strength in C 1618 fatty alcohol, Evonik Industries, INCI: Distearoylethyl Dimonium Chloride, Cetearyl Alcohol), an ester quat. The comparative formulation V4b comprises, as conditioning compound, VARISOFT® BT 85 (85% strength in isopropanol, Evonik Industries, INCI: Behentrimonium Chloride), an alkyl quat which is known for its considerable reduction in the combing forces even in the case of long rinsing times.

TABLE 4

Hair rinse formulations for testing the hair conditioning properties

| Formulation Examples | C0b | 1b | V2b | V3b | V4b | 5b | 6b |
|---|---|---|---|---|---|---|---|
| TEGINACID C, Evonik Industries (INCI: Ceteareth-25) | 0.5% | 0.5% | 0.5% | 0.5% | 0.5% | 0.5% | 0.5% |
| TEGO Alkanol 1618, Evonik Industries (INCI: Cetearyl alcohol) | 4% | 4% | 4% | 4% | 4% | 4% | 4% |
| Synthesis Example 1 (100%) | | 1% | | | | | |
| Synthesis Example 2 (80% strength in isopropanol) | | | 1.25% | | | | |
| Synthesis Example 3a | | | | | | 1% | |
| Synthesis example 3b | | | | | | | 1% |
| Varisoft EQ 65 Pellets (65% strength in C16 fatty alcohol), Evonik Industries (INCI: Distearoylethyl Dimonium Chloride, Cetearyl Alcohol) | | | | 1.53% | | | |
| VARISOFT BT 85, (85% strength in isopropanol), Evonik Industries (INCI: Behentrimonium Chloride) | | | | | 1.18% | | |
| Water, demineralized | | | | to 100.0 | | | |
| Citric acid | | | | to pH 4.0 | | | |

Example 6

Antistatic Finishing of Keratin Fibres

To test the antistatic behaviour, the shadow silhouette method was used.

The pretreated hair tresses described above, a plastic comb, a spotlight and a projection field marked with concentric semicircles were used.

The experiments were carried out under standardized climatic conditions. The hair tress was hung up at a distance of 15 cm from the projection field. The spotlight was positioned at a distance of 145 cm from the hair tress so that a shadow fell on the projection field.

The hair tress was then combed five times in succession using the comb. The electrostatic charging was measured via the shadow silhouette by marking the two outer points of the shadow and determining the distance between them. The smaller the shadow area, the more effective the antistatic effect.

Result:

| Formulation | Distance |
|---|---|
| C0a | 16 cm |
| 1a | 6 cm |

Example 7

Influence on Viscosity by Fatty Alcohol

|  | d1 | d2 | d3 | d4 | d5 | d6 | d7 | d8 |
|---|---|---|---|---|---|---|---|---|
| TEGO ® Alkanol 1618, Evonik Nutrition & Care GmbH (INCI: Cetearyl Alcohol) | 3.40 |  | 3.40 |  | 3.40 |  | 3.40 |  |
| TEGO ® Alkanol 16, Evonik Nutrition & Care GmbH (INCI: Cetyl Alcohol) |  | 1.22 |  | 1.22 |  | 1.22 |  | 1.22 |
| TEGO ® Alkanol 18, Evonik Nutrition & Care GmbH (INCI: Stearyl Alcohol) |  | 1.84 |  | 1.84 |  | 1.84 |  | 1.84 |
| Oleyl Alcohol (85% strength) |  | 0.34 |  | 0.34 |  | 0.34 |  | 0.34 |
| TEGINACID ® C, Evonik Nutrition & Care GmbH (INCI: Ceteareth-25) | 0.50 | 0.50 | 0.50 | 0.50 | 0.50 | 0.50 | 0.50 | 0.50 |
| Inventive example 1 | 0.30 | 0.30 | 0.50 | 0.50 | 0.60 | 0.60 | 0.75 | 0.75 |
| Water | 95.90 | 95.80 | 95.70 | 95.60 | 95.60 | 95.50 | 95.45 | 95.35 |
| Preservative, Perfume | q.s. | q.s. | q.s. | q.s. | q.s. | q.s. | q.s. | q.s. |
| Initial viscosity [/mPas] | 7100 | 8400 | 9700 | 11100 | 7300 | 10300 | 6500 | 10400 |
| pH (4.0-4.5) | 4.0 | 4.0 | 4.0 | 4.0 | 4.0 | 4.0 | 4.0 | 4.0 |

Example 8

Influence on Viscosity by Fatty Alcohol Mixture

|  | b1 | b2 | b3 | b4 | b5 |
|---|---|---|---|---|---|
| TEGO ® Alkanol 1618; Evonik Nutrition & Care GmbH (INCI: Cetearyl Alcohol) | 5.00 | | | | |
| TEGO ® Alkanol 16; Evonik Nutrition & Care GmbH (INCI: Cetyl Alcohol) | | 5.00 | | 3.00 | 1.8 |
| TEGO ® Alkanol 18, Evonik Nutrition & Care GmbH (INCI: Stearyl Alcohol) | | | 5.00 | 1.00 | 2.7 |
| Oleyl Alcohol (85% strength) | | | | 1.00 | 0.50 |
| TEGINACID ® C, Evonik Nutrition & Care GmbH (INCI: Ceteareth-25) | 0.50 | 0.50 | 0.50 | 0.50 | 0.50 |
| Inventive example 1 | 1.00 | 1.00 | 1.00 | 1.00 | 1.00 |
| Water | 93.50 | 93.50 | 93.50 | 93.50 | 93.50 |
| Preservative, Perfume | q.s. | q.s. | q.s. | q.s. | q.s. |
| Initial viscosity [/mPas] | 5500 | 2540 | <500 | 6200 | 7800 |
| pH | 4.5 | 4.5 | 4.50 | 4.5 | 4.5 |

Example 9

Sensoric Results of the Formulations from Example 9

These experiments were carried out analogously to example 5.

a) 1 Min Rinsing Time

TABLE 5a

Results of conditioning of hair at 1 min rinsing time

|  | Wet combability | Wet feel | Dry combability | Dry feel |
|---|---|---|---|---|
| Inventive formulation b1 | 5 | 4.5 | 4.5 | 5 |
| Inventive formulation b5 | 5 | 4.5 | 4.5 | 5 |
| Control C0a | 2 | 2 | 3 | 3 | b) 3 Min Rinsing Time

TABLE 5b

Results of conditioning of hair at 3 min rinsing time

|  | Wet combability | Wet feel | Dry combability | Dry feel |
|---|---|---|---|---|
| Inventive formulation b1 | 4.5 | 4.5 | 4 | 4 |
| Inventive formulation b5 | 4.5 | 4.5 | 4 | 4.5 |
| Kontrolle C0a | 2 | 2 | 2.5 | 2.5 |

The results in Table 5a show that the inventive formulation b5 at 1 min rinsing time has very good conditioning properties, which are equivalent to inventive formulation b1.

The results in Table 5b show that the inventive formulation b5 at 3 min rinsing time also has very good conditioning properties, which are equivalent to inventive formulation b1.

Example 10

Results of Combing Force Measurements

In FIG. 1, the results of the combing force measurements of the experiments at 3 min rinsing time carried out as described above, are compared with inventive formulation b5 and formulation b1.

The results in FIG. 1 show that inventive formulation b5 at 3 min rinsing time has a comparably good reduction of the combing forces as formulation b1.

Example 11

Figure 2:
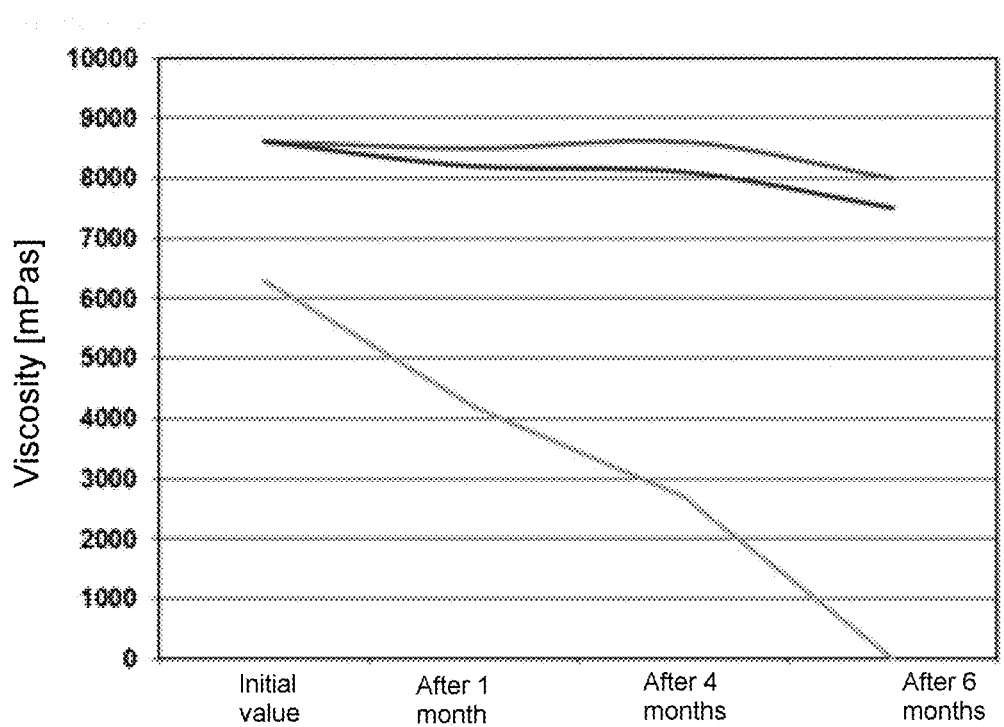
FIG. 2 illustrates the storage stability of formulations e2 and e1; upper curve e2 at 25° C., middle curve e2 at 45° C. and lower curve e1 at 25° C.

Long-Term Stability of the Formulations with Fatty Alcohol Mixture 200 g of the respective formulations were filled in a 250 ml powder glass bottle and stored for several months in a climate cabinet at 25° C. and 45° C. The viscosity was measured in each case after the preparation, after one month's storage, after 4 months' storage, and after 6 months' storage at 25° C. (Brookfield, RVDV, Spindle T-C, 30 rpm) The result are shown in FIG. 2.

|  | e1 | e2 |
|---|---|---|
| TEGO ® Alkanol 1618; Evonik Nutrition & Care GmbH (INCI: Cetearyl Alcohol) | 5.00 | |
| TEGO ® Alkanol 16; Evonik Nutrition & Care GmbH (INCI: Cetyl Alcohol) | | 1.80 |
| TEGO ® Alkanol 18; Evonik Nutrition & Care GmbH (INCI: Stearyl Alcohol) | | 2.70 |
| Oleyl Alcohol (85% strength) | | 0.50 |
| TEGINACID ® C; Evonik Nutrition & Care GmbH (INCI: Ceteareth-25) | 0.50 | 0.50 |
| Inventive example 1 | 1.00 | 1.00 |
| Water | 93.50 | 93.50 |
| Preservative, Perfume | q.s. | q.s. |
| Initial viscosity [/mPas] | 6300 | 8600 |
| pH | 4.0 | 4.0 |

Example Formulations

Formulation Example 1)

Pearlized Shampoo

| | |
|---|---|
| TEXAPON ® NSO, Cognis, 28% strength (INCI: Sodium Laureth Sulphate) | 32.25% |
| Inventive Example 1 | 0.25% |
| Perfume | 0.25% |
| Water | 55.25% |

-continued

| | |
|---|---|
| TEGO ® Betain F 50, Evonik Industries AG, 38% strength (INCI: Cocamidopropyl Betaine) | 8.00% |
| TEGO ® Pearl N 300 Evonik Industries AG (INCI: Glycol Distearate; Laureth-4; Cocamidopropyl Betaine) | 2.00% |
| ANTIL ® 171 Evonik Industries AG (INCI: PEG-18 Glyceryl Oleate/Cocoate) | 1.50% |
| NaCl | 0.50% |
| Preservative | q.s. |

Formulation Example 2)

Rinse-Off Conditioner

| | |
|---|---|
| Water | 92.0% |
| TEGINACID ® C, Evonik Industries AG (INCI: Ceteareth-25) | 0.5% |
| Inventive Example 1 | 2.50% |
| TEGO ® Alkanol 1618, Evonik Industries AG (INCI: Cetearyl Alcohol) | 5.00% |
| Preservative, perfume | q.s. |

Formulation Example 3)

Rinse-Off Conditioner

| | |
|---|---|
| Water | 91.0% |
| Inventive Example 1 | 2.00% |
| VARISOFT ® BT 85, Evonik Industries AG (INCI: Behentrimonium Chloride) | 2.00% |
| TEGO ® Alkanol 1618, Evonik Industries AG (INCI: Cetearyl Alcohol) | 5.00% |
| Preservative, perfume | q.s. |

Formulation Example 4)

Rinse-Off Conditioner

| | |
|---|---|
| Water | 90.20% |
| Inventive Example 1 | 2.00% |
| VARISOFT ® EQ 65, Evonik Industries AG (INCI: Distearoyl Dimonium Chloride, Cetearyl Alcohol) | 2.00% |
| TEGO ® Alkanol 1618, Evonik Industries AG (INCI: Cetearyl Alcohol) | 5.80% |
| Preservative, perfume | q.s. |

Formulation Example 5)

Rinse-Off Conditioner

| | |
|---|---|
| Water | 89.20% |
| TEGINACID ® C, Evonik Industries AG(INCI: Ceteareth-25) | 0.5% |
| VARISOFT ® EQ 65, Evonik Industries AG (INCI: Distearoyl Dimonium Chloride, Cetearyl Alcohol) | 2.00% |
| Inventive Example 1 | 2.00% |
| ABIL ® Quat 3272, Evonik Industries AG (INCI: Quaternium-80) | 1.30% |
| TEGO ® Alkanol 1618, Evonik Industries AG (INCI: Cetearyl Alcohol) | 5.00% |
| Preservative, perfume | q.s. |

Formulation Example 6)

Rinse-Off Conditioner

| | |
|---|---|
| TEGINACID ® C, Evonik Industries AG (INCI: Ceteareth-25) | 0.50% |
| TEGO ® Alkanol 16, Evonik Industries AG (INCI: Cetyl Alcohol) | 2.00% |
| TEGO ® Amid S 18, Evonik Industries AG (INCI: Stearamidopropyl Dimethylamine) | 1.00% |
| Inventive Example 1 | 1.50% |
| Propylene glycol | 2.00% |
| Citric acid monohydrate | 0.30% |
| Water | 92.70% |
| Preservative, perfume | q.s. |

Formulation Example 7)

Rinse-Off Conditioner

| | |
|---|---|
| TEGINACID ® C, Evonik Industries AG (INCI: Ceteareth-25) | 0.50% |
| TEGO ® Alkanol 16, Evonik Industries AG (INCI: Cetyl Alcohol) | 5.00% |
| TEGOSOFT ® DEC, Evonik Industries AG (INCI: Diethylhexyl Carbonate) | 1.00% |
| Inventive Example 1 | 1.50% |
| Water | 89.20% |
| TEGO ® Cosmo C 100, Evonik Industries AG (INCI: Creatine) | 0.50% |
| Propylene glycol | 2.00% |
| Citric acid monohydrate | 0.30% |
| Preservative, perfume | q.s. |

Formulation Example 8)

Leave-In Conditioner Spray

| | |
|---|---|
| Lactic acid, 80% | 0.40% |
| Water | 95.30% |
| Inventive Example 1 | 1.20% |
| TEGIN ® G 1100 Pellets, Evonik Industries AG (INCI: Glycol Distearate) | 0.60% |
| TEGO ® Care PS, Evonik Industries AG (INCI: Methyl Glucose Sesquistearate) | 1.20% |
| TEGOSOFT ® DEC, Evonik Industries AG (INCI: Diethylhexyl Carbonate) | 1.30% |
| Preservative, perfume | q.s. |

Formulation Example 9)

Leave-In Conditioner Spray

| | |
|---|---|
| Lactic acid, 80% | 0.40% |
| Water | 95.30% |
| TEGO ® Amid S 18, Evonik Industries AG (INCI: Stearamidopropyl dimethylamine) | 1.20% |
| Inventive Example 1 | 0.30% |
| TEGIN ® G 1100 Pellets, Evonik Industries AG (INCI: Glycol Distearate) | 0.90% |
| TEGO ® Care PS, Evonik Industries AG (INCI: Methyl Glucose Sesquistearate) | 1.60% |
| TEGOSOFT ® DEC, Evonik Industries AG (INCI: Diethylhexyl Carbonate) | 0.30% |
| Preservative, perfume | q.s. |

Formulation Example 10)

Leave-In Conditioner Spray

| | |
|---|---|
| TAGAT ® CH-40, Evonik Industries AG (INCI: PEG-40 Hydrogenated Castor Oil) | 2.20% |
| Ceramide VI, Evonik Industries AG (INCI: Ceramide 6 II) | 0.05% |
| Perfume | 0.20% |
| Water | 90.95% |
| Inventive Example 1 | 0.30% |
| LACTIL ®, Evonik Industries AG (INCI: Sodium Lactate; Sodium PCA; Glycine; Fructose; Urea; Niacinamide; Inositol; Sodium benzoate; Lactic Acid) | 2.00% |
| TEGO ® Betain F 50, Evonik Industries AG, 38% (INCI: Cocamidopropyl Betaine) | 2.30% |
| Citric acid (10% in water) | 2.00% |

Formulation Example 11)

Leave-in Conditioner Foam

| | |
|---|---|
| Inventive Example 1 | 0.30% |
| TAGAT ® CH-40, Evonik Industries AG (INCI: PEG-40 Hydrogenated Castor Oil) | 1.0% |
| Perfume | 0.30% |
| TEGO ® Betain 810, Evonik Industries AG (INCI: Capryl/Capramidopropyl Betaine) | 2.00% |
| Water | 94.00% |
| TEGO ® Cosmo C 100, Evonik Industries AG (INCI: Creatine) | 0.50% |
| TEGOCEL ® HPM 50, Evonik Industries AG (INCI: Hydroxypropyl Methylcellulose) | 0.30% |
| VARISOFT ® 300, Evonik Industries AG (INCI: Cetrimonium Chloride) | 1.0% |
| LACTIL ® Evonik Industries AG (INCI: Sodium Lactate; Sodium PCA; Glycine; Fructose; Urea; Niacinamide; Inositol; Sodium benzoate; Lactic Acid) | 0.50% |
| Citric acid, 30% | 0.10% |
| Preservative | q.s. |

Formulation Example 12)

Strong Hold Styling Gel

| | |
|---|---|
| TEGO ® Carbomer 141, Evonik Industries AG (INCI: Carbomer) | 1.20% |
| Water | 66.70% |
| NaOH, 25% | 2.70% |
| PVP/VA W-735, ISP (INCI: PVP/VA Copolymer) | 16.00% |
| Inventive Example 1 | 0.30% |
| Denatured alcohol | 10.50% |
| TAGAT ® O 2 V, Evonik Industries AG (INCI: PEG-20 Glyceryl Oleate) | 2.00% |
| Perfume | 0.30% |
| ABIL ® B 88183, Evonik Industries AG (INCI: PEG/PPG-20/6 Dimethicone) | 0.30% |
| Preservative | q.s. |

Formulation Example 13)

Bodycare Product

| | |
|---|---|
| TEXAPON ® NSO, Cognis, 28% strength (INCI: Sodium Laureth Sulfate) | 30.00% |
| TEGOSOFT ® PC 31, Evonik Industries AG (INCI: Polyglyceryl-3 Caprate) | 0.70% |
| Inventive Example 1 | 0.30% |
| Perfume | 0.30% |
| Water | 53.90% |
| TEGOCEL ® HPM 4000, Evonik Industries AG (INCI: Hydroxypropyl Methylcellulose) | 0.30% |
| REWOTERIC ® AM C, Evonik Industries AG, 32% strength (INCI: Sodium Cocoamphoacetate) | 10.00% |
| Citric acid monohydrate | 0.50% |
| REWODERM ® LI S 80, Evonik Industries AG (INCI: PEG-200 Hydrogenated Glyceryl Palmate; PEG-7 Glyceryl Cocoate) | 2.00% |
| TEGO ® Pearl N 300, Evonik Industries AG (INCI: Glycol Distearate; Laureth-4; Cocamidopropyl Betaine) | 2.00% |

Formulation Example 14)

Mild Foam Bath

| | |
|---|---|
| TEXAPON ® NSO, Cognis, 28% strength (INCI: Sodium Laureth Sulfate) | 27.00% |
| REWOPOL ® SB FA 30, Evonik Industries AG, 40% strength (INCI: Disodium Laureth Sulfosuccinate) | 12.00% |
| TEGOSOFT ® LSE 65 K SOFT, Evonik Industries AG (INCI: Sucrose Cocoate) | 2.00% |
| Water | 39.00% |
| REWOTERIC ® AM C, Evonik Industries AG, 32% strength (INCI: Sodium Cocoamphoacetate) | 13.00% |
| Inventive Example 1 | 0.40% |
| Citric acid (30% in water) | 3.00% |
| ANTIL ® 171 Evonik Industries AG (INCI: PEG-18 Glyceryl Oleate/Cocoate) | 1.60% |
| TEGO ® Pearl N 300 Evonik Industries AG (INCI: Glycol Distearate; Laureth-4; Cocamidopropyl Betaine) | 2.00% |

Formulation Example 15)

Rinse-Off Conditioner

| | |
|---|---|
| Water | 89.20% |
| Inventive Example 1 | 3.00% |
| ABIL ® OSW 5, Evonik Industries AG (INCI: Cyclopentasiloxane; Dimethiconol) | 1.80% |
| TEGO ® Alkanol 1618, Evonik Industries AG, (INCI: Cetearyl Alcohol) | 6.00% |
| Preservative, perfume | q.s. |

Formulation Example 16)

Rinse-Off Conditioner

| | |
|---|---|
| Water | 89.20% |
| TEGINACID ® C, Evonik Industries AG (INCI: Ceteareth-25) | 0.5% |
| VARISOFT ® EQ 65, Evonik Industries AG (INCI: Distearoyl Dimonium Chloride, Cetearyl Alcohol) | 1.50% |
| Inventive Example 1 | 2.00% |
| ABIL ® Soft AF 100, Evonik Industries AG (INCI: Methoxy PEG/PPG-7/3 Aminopropyl Dimethicone) | 1.00% |
| TEGO ® Alkanol 1618, Evonik Industries AG, (INCI: Cetearyl Alcohol) | 5.80% |
| Preservative, perfume | q.s. |

Formulation Example 17)

Rinse-Off Conditioner

| | |
|---|---|
| Water | 91.50% |
| TEGINACID ® C, Evonik Industries AG (INCI: Ceteareth-25) | 0.5% |
| Inventive Example 1 | 2.00% |
| SF 1708, Momentive (INCI: Amodimethicone) | 1.00% |
| TEGO ® Alkanol 1618, Evonik Industries AG (INCI: Cetearyl Alcohol) | 5.00% |
| Preservative, perfume | q.s. |

Formulation Example 18)

2 in 1 Shampoo & Intensive Conditioner

| | |
|---|---|
| Water | 28.00% |
| Jaguar C-162 (Hydroxypropyl Guar Hydroxypropyltimonium Chloride) | 0.5% |
| VARISOFT ® BT 85, Evonik Industries AG (INCI: Behentrimonium Chloride) | 0.50% |
| Inventive Example 1 | 0.50% |
| TEGO ® Alkanol 1618, Evonik Industries AG (INCI: Cetearyl Alcohol) | 1.00% |
| TEGIN ® G 1100 Pellets, Evonik Industries AG (INCI: Glycol Distearate) | 0.80% |
| Sodium laureth sulphate, 28% | 39.0% |
| Petrolatum | 1.0% |
| ABIL ®T-Quat 60, Evonik Industries AG (INCI: Silicone Quaternium-22) | 1.3% |
| REWOTERIC ® AM C, Evonik Industries AG (INCI: Sodium Cocoamphoacetate) | 17.50% |
| Citric acid (20%) | 6.3% |
| ANTIL ® SPA 80, Evonik Industries AG (INCI: Isostearamide MIPA; Glyceryl Laurate) | 2.20% |
| NaCl | 1.0% |
| REWODERM ® LI S 80, Evonik Industries AG (INCI: PEG-200 Hydrogenated Glyceryl Palmate; PEG-7 Glyceryl Cocoate) | 1.0% |
| Preservative, perfume | q.s. |

Formulation Example 19)

Pet Care—Conditioner

| | |
|---|---|
| TEGO ® Alkanol 1618, Evonik Industries AG (INCI: Cetearyl Alcohol) | 4.0% |
| TEGINACID ® C, Evonik Industries AG (INCI: Ceteareth-25) | 0.5% |
| VARISOFT ® BT 85, Evonik Industries AG (INCI: Behentrimonium Chloride) | 2.0% |
| Inventive Example 1 | 1.0% |
| TEGIN ® M, Evonik Industries AG (INCI: Glyceryl Stearate) | 0.5% |
| Water | 93.0% |
| Preservative, perfume | q.s. |

Formulation Example 20)

In-Shower Hair and Body Conditioner (O/W Emulsion)

| | |
|---|---|
| ABIL ® Soft AF 100, Evonik Industries AG (INCI: Methoxy PEG/PPG-7/3 Aminopropyl Dimethicone) | 0.5% |
| Inventive Example 1 | 1.0% |
| VARISOFT ® BT 85, Evonik Industries AG (INCI: Behentrimonium Chloride) | 0.5% |
| TEGO ® Alkanol 16, Evonik Industries AG (INCI: Cetyl Alcohol) | 2.0% |
| *Simmondsia chinensis* (jojoba) seed oil | 0.5% |
| Water | 93.5% |
| Glycerol | 2.0% |
| Panthenol | 0.2% |
| Preservative, perfume | q.s. |

Formulation Example 21)

Hot Oil Treatment

| | |
|---|---|
| Water | 96.5 |
| Polyquaternium- 10 | 1.0% |
| Hydroxyethylcellulose | 0.5% |
| Inventive Example 1 | 1.0% |
| VARISOFT ® BT 85, Evonik Industries AG (INCI: Behentrimonium Chloride) | 1.0% |
| Lauramide DEA | 1.0% |
| Citric acid, (30%) | q.s. |
| Preservative, perfume | q.s. |

Formulation Example 22)

Strong Conditioning Hair Rinse for Damaged Hair

| | |
|---|---|
| VARISOFT ® BT 85, Evonik Industries AG (INCI: Behentrimonium Chloride) | 0.5% |
| Inventive Example 1 | 0.5% |
| COSMOFERM ® Mix III, Evonik Industries AG (INCI: Isocetyl Alcohol; Ceramide NP; Cetyl Alcohol) | 2.0% |
| TEGINACID ® C, Evonik Industries AG (INCI: Ceteareth- 25) | 0.5% |
| ABIL ® Soft AF 100, Evonik Industries AG (INCI: Methoxy PEG/PPG-7/3 Aminopropyl Dimethicone) | 0.3% |
| TEGO ® Alkanol 16, Evonik Industries AG (INCI: Cetyl Alcohol) | 2.0% |
| TEGIN ® M, Evonik Industries AG (INCI: Glyceryl Stearate) | 1.0% |
| ABIL ® OSW 5, Evonik Industries AG (INCI: Cyclopentasiloxane; Dimethiconol) | 7.5% |
| Water | 86.2% |
| Preservative, perfume | q.s. |

Formulation Example 23)

Conditioning Hair Rinse for Coloured Hair

| | |
|---|---|
| TEGIN ® M, Evonik Industries AG (INCI: Glyceryl Stearate) | 2.0% |
| TEGO ® Alkanol 1618, Evonik Industries AG (INCI: Cetearyl Alcohol) | 3.0% |
| TEGO ® Amid S 18, Evonik Industries AG (INCI: Stearamidopropyl Dimethylamine) | 0.7% |
| VARISOFT ® BT 85, Evonik Industries AG (INCI: Behentrimonium Chloride) | 0.8% |
| Inventive Example 1 | 0.8% |
| VARISOFT ®W 575 PG, Evonik Industries AG (INCI: Quaternium-87) | 0.9% |
| Water | 90.9% |
| 1,2-Propylene glycol (Propylene Glycol) | 1.0% |
| Citric acid (20%) | 0.7% |
| Preservative, perfume | q.s. |

Formulation Example 24)

Conditioning Hair Rinse

| | |
|---|---|
| TEGO ® Alkanol 1618, Evonik Industries AG (INCI: Cetearyl Alcohol) | 5.0% |
| TEGO ® Care 450, Evonik Industries AG (INCI: Polyglyceryl-3 Methylglucose Distearate) | 1.0% |
| Inventive Example 1 | 1.0% |
| Water | 92.55% |
| Preservative | 0.45% |

Formulation Example 25)

Conditioning Hair Rinse

| | |
|---|---|
| TEGO ® Alkanol 1618, Evonik Industries AG (INCI: Cetearyl Alcohol) | 5.0% |
| TEGO ® Care CG 90, Evonik Industries AG (INCI: Cetearyl Glucoside) | 1.0% |
| Inventive Example 1 | 1.0% |
| Water | 92.55% |
| Preservative | 0.45% |

Formulation Example 26)

Conditioning Hair Rinse

| | |
|---|---|
| TEGO ® Alkanol 1618, Evonik Industries AG (INCI: Cetearyl Alcohol) | 5.0% |
| TEGO ® Care PSC 3, Evonik Industries AG (INCI: Polyglyceryl-3 Dicitrate/Stearate) | 1.0% |
| Inventive Example 1 | 1.0% |
| Water | 92.55% |
| Preservative | 0.45% |

Formulation Example 27)

Conditioning Hair Rinse

| | |
|---|---|
| TEGO ® Alkanol 1618, Evonik Industries AG (INCI: Cetearyl Alcohol) | 5.0% |
| TEGO ® Acid S 40 P, Evonik Industries AG (INCI: PEG-40 Stearate) | 1.0% |
| Inventive Example 1 | 1.0% |
| Water | 92.55% |
| Preservative | 0.45% |

Formulation Example 28)

Conditioning Hair Rinse

| | |
|---|---|
| TEGO ® Alkanol 1618, Evonik Industries AG (INCI: Cetearyl Alcohol) | 5.0% |
| ABIL ® Care 85, Evonik Industries AG (INCI: Bis-PEG/PPG-16/16 PEG/PPG-16/16 Dimethicone; Caprylic/Capric Triglyceride) | 1.0% |
| Inventive Example 1 | 1.0% |
| Water | 92.55% |
| Preservative | 0.45% |

Formulation Example 29)

Conditioning Hair Rinse

| | |
|---|---|
| TEGO ® Alkanol 1618, Evonik Industries AG (INCI: Cetearyl Alcohol) | 5.0% |
| ABIL ® Care XL 80, Evonik Industries AG (INCI: Bis-PEG/PPG-20/5 PEG/PPG-20/5 Dimethicone; Methoxy PEG/PPG-25/4 Dimethicone; Caprylic/Capric Triglyceride) | 1.0% |
| Inventive Example 1 | 1.0% |
| Water | 92.55% |
| Preservative | 0.45% |

Formulation Example 30)

Conditioning Hair Rinse

| | |
|---|---|
| TEGO ® Alkanol 1618, Evonik Industries AG (INCI: Cetearyl Alcohol) | 5.0% |
| TEGO ® Alkanol CS 20 P, Evonik Industries AG (INCI: Ceteareth-20) | 0.5% |
| VARISOFT ® EQ 65, Evonik Industries AG (INCI: Distearoylethyl Dimonium Chloride; Cetearyl Alcohol) | 2.0% |
| Inventive Example 1 | 1.3% |
| ABIL ® Quat 3474, Evonik Industries AG (INCI: Quaternium-80) | 0.5% |
| EDTA | 0.02% |
| Water | 90.68% |
| Preservative, perfume | q.s. |

Formulation Example 31)

Conditioning Hair Rinse

| | |
|---|---|
| TEGO ® Alkanol 1618, Evonik Industries AG (INCI: Cetearyl Alcohol) | 5.0% |
| TEGO ® Alkanol CS 20 P, Evonik Industries AG (INCI: Ceteareth-20) | 0.5% |
| VARISOFT ® BT 85, Evonik Industries AG (INCI: Behentrimonium Chloride) | 2.0% |
| Inventive Example 1 | 1.3% |
| ABIL ® Quat 3474, Evonik Industries AG (INCI: Quaternium-80) | 0.5% |
| EDTA | 0.02% |
| Water | 90.68% |
| Preservative, perfume | q.s. |

Formulation Example 32)

Conditioning Hair Rinse

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Inventive Example 1 | 1.0% |
| Water | 91.0% |
| Preservative, perfume | q.s. |

Formulation Example 33)

Conditioning Hair Rinse

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Inventive Example 1 | 1.0% |
| ABIL ® ME 45, Evonik Industries AG (INCI: Silicone Quaternium-22; Polyglyceryl-3 Caprate; Dipropylene Glycol; Cocamidopropyl Betaine) | 1.7% |
| Water | 89.3% |
| Preservative, perfume | q.s. |

Formulation Example 34)

Conditioning Hair Rinse

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Inventive Example 1 | 1.0% |
| Amodimethicone | 1.0% |
| Water | 90.0% |
| Preservative, perfume | q.s. |

Formulation Example 35)

Conditioning Hair Rinse

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Inventive Example 1 | 1.0% |
| ABIL ® Soft AF 300, Evonik Industries AG (INCI: Aminopropyl Dimethicone) | 1.0% |
| Water | 90.0% |
| Preservative, perfume | q.s. |

Formulation Example 36)

Conditioning Hair Rinse

| | |
|---|---|
| TEGO ® Alkanol 16, Evonik Industries AG (INCI: Cetyl Alcohol) | 5.0% |
| TEGINACID ® C, Evonik Industries AG (INCI: Ceteareth-25) | 0.5% |
| Inventive Example 1 | 1.0% |
| Water | 93.5% |
| Preservative, perfume | q.s. |

Formulation Example 37)

Conditioning Hair Rinse

| | |
|---|---|
| TEGO ® Alkanol 16, Evonik Industries AG (INCI: Cetyl Alcohol) | 5.0% |
| TEGINACID ® C, Evonik Industries AG (INCI: Ceteareth-25) | 0.5% |
| TEGO ® Amid S 18, Evonik Industries AG (INCI: Stearamidopropyl Dimethylamine) | 0.5% |
| Inventive Example 1 | 0.5% |
| Water | 93.5% |
| Preservative, perfume | q.s. |

Formulation Example 38)

Conditioning Hair Rinse

| | |
|---|---|
| TEGO ® Alkanol 18, Evonik Industries AG (INCI: Stearyl Alcohol) | 5.0% |
| TEGINACID ® C, Evonik Industries AG (INCI: Ceteareth-25) | 0.5% |
| TEGO ® Amid S 18, Evonik Industries AG (INCI: Stearamidopropyl Dimethylamine) | 0.5% |
| Inventive Example 1 | 0.5% |
| Water | 93.5% |
| Preservative, perfume | q.s. |

Formulation Example 39)

Conditioning Hair Rinse

| | |
|---|---|
| TEGO ® Alkanol 18, Evonik Industries AG (INCI: Stearyl Alcohol) | 5.0% |
| TEGINACID ® C, Evonik Industries AG (INCI: Ceteareth-25) | 0.5% |
| Inventive Example 1 | 1.0% |
| Water | 93.5% |
| Preservative, perfume | q.s. |

Formulation Example 40)

Conditioning Hair Rinse

| | |
|---|---|
| TEGO ® Alkanol 1618, Evonik Industries AG (INCI: Cetearyl Alcohol) | 7.0% |
| TEGO ® Alkanol S 20 P, Evonik Industries AG (INCI: Steareth-20) | 1.0% |
| Inventive Example 1 | 1.0% |
| Water | 91.0% |
| Preservative, perfume | q.s. |

Formulation Example 41)

Conditioning Hair Rinse

| | |
|---|---|
| TEGO ® Alkanol 1618, Evonik Industries AG (INCI: Cetearyl Alcohol) | 7.0% |
| TEGO ® Alkanol L 23 P, Evonik Industries AG (INCI: Laureth-23) | 1.0% |
| Inventive Example 1 | 1.0% |
| Water | 91.0% |
| Preservative, perfume | q.s. |

Formulation Example 42)

Rinse-Off Conditioner

| | |
|---|---|
| Water | 91.0% |
| Inventive Example 3a | 2.00% |
| VARISOFT ® BT 85, Evonik Industries AG (INCI: Behentrimonium Chloride) | 2.00% |
| TEGO ® Alkanol 1618, Evonik Industries AG (INCI: Cetearyl Alcohol) | 5.00% |
| Preservative, perfume | q.s. |

Formulation Example 43)

Rinse-Off Conditioner

| | |
|---|---|
| Water | 90.20% |
| Inventive Example 3a | 2.00% |
| VARISOFT ® EQ 65, Evonik Industries AG (INCI: Distearoyl Dimonium Chloride, Cetearyl Alcohol) | 2.00% |
| TEGO ® Alkanol 1618, Evonik Industries AG, (INCI: Cetearyl Alcohol) | 5.80% |
| Preservative, perfume | q.s. |

Formulation Example 44)

Rinse-Off Conditioner

| | |
|---|---|
| Water | 89.20% |
| TEGINACID ® C, Evonik Industries AG (INCI: Ceteareth-25) | 0.5% |
| VARISOFT ® EQ 65, Evonik Industries AG (INCI: Distearoyl Dimonium Chloride, Cetearyl Alcohol) | 2.00% |
| Inventive Example 3a | 2.00% |
| ABIL ® Quat 3272, Evonik Industries AG (INCI: Quaternium-80) | 1.30% |
| TEGO ® Alkanol 1618, Evonik Industries AG (INCI: Cetearyl Alcohol) | 5.00% |
| Preservative, perfume | q.s. |

Formulation Example 45)

Conditioning Hair Rinse

| | |
|---|---|
| TEGO ® Alkanol 1618, Evonik Industries AG (INCI: Cetearyl Alcohol) | 7.0% |
| TEGO ® Alkanol S 20 P, Evonik Industries AG (INCI: Steareth-20) | 1.0% |
| Inventive Example 3a | 1.0% |
| Water | 91.0% |
| Preservative, perfume | q.s. |

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed as new is:

1. A cosmetic formulation comprising:
0.2 to 25% by weight of at least one ester quat of general formula I)

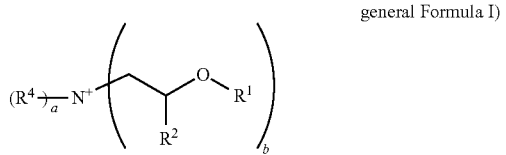

general Formula I)

wherein:
$R^1$ is an acyl residue of erucic acid;
$R^2$ is methyl;
$R^4$ is once methyl and once ethyl;
a=2; and
b=2;
and 40 to 99.8% by weight of water, wherein the percentages by weight refer to the overall formulation.

2. The cosmetic formulation according to claim 1, wherein no fatty acids or fatty acid salts are present.

3. The cosmetic formulation according to claim 1, further comprising:
0.5 to 20% by weight of at least one fatty alcohol,
where the percentages by weight refer to the total formulation.

4. The cosmetic formulation according to claim 3, wherein said fatty alcohol is selected from octanol, decanol, lauryl alcohol, isolauryl alcohol, anteisolauryl alcohol, myristyl alcohol, isomyristyl alcohol, cetyl alcohol, palmoleyl alcohol, stearyl alcohol, isostearyl alcohol, anteisostearyl alcohol, eicosanol, petroselinyl alcohol, Guerbet alcohol, arachyl alcohol, gadoleyl alcohol, behenyl alcohol, erucyl alcohol, hectacosanol, octacosanol, and melissyl alcohol, and mixtures thereof.

5. The cosmetic formulation according to claim 1, further comprising: at least one counterion to the compound of general formula I) selected from chloride, bromide, iodide, alkyl sulphate, alkylsulphonate, triflate, tosylate, phosphate, sulphate, hydrogensulphate, lactate, glycolate, acetate and citrate.

* * * * *